United States Patent
Chen (10) Patent No.: US 10,513,597 B2
(45) Date of Patent: Dec. 24, 2019

(54) MEDICAL DEVICE AND PLASTICIZED NYLON MATERIAL

(71) Applicant: Medtronic Vascular, Inc., Santa Rosa, CA (US)

(72) Inventor: Mingfei Chen, Santa Rosa, CA (US)

(73) Assignee: Medtronic Vascular, Inc., Santa Rosa, CA (US)

( * ) Notice: Subject to any disclaimer, the term of this patent is extended or adjusted under 35 U.S.C. 154(b) by 36 days.

(21) Appl. No.: 15/642,758

(22) Filed: Jul. 6, 2017

(65) Prior Publication Data
US 2018/0009966 A1 Jan. 11, 2018

Related U.S. Application Data

(60) Provisional application No. 62/359,323, filed on Jul. 7, 2016.

(51) Int. Cl.
*C08K 5/20* (2006.01)
*A61L 29/06* (2006.01)
*A61L 29/14* (2006.01)
*A61L 31/06* (2006.01)
*A61L 31/14* (2006.01)
*C08J 5/18* (2006.01)
*C08K 5/00* (2006.01)

(52) U.S. Cl.
CPC .............. *C08K 5/20* (2013.01); *A61L 29/06* (2013.01); *A61L 29/141* (2013.01); *A61L 31/06* (2013.01); *A61L 31/141* (2013.01); *C08J 5/18* (2013.01); *C08J 2377/02* (2013.01); *C08K 5/0016* (2013.01)

(58) Field of Classification Search
CPC .................................................. C08K 5/0016
See application file for complete search history.

(56) References Cited

U.S. PATENT DOCUMENTS

| | | | |
|---|---|---|---|
| 4,863,991 A * | 9/1989 | Poppe | C08G 69/265 524/606 |
| 5,534,575 A | 7/1996 | Foster et al. | |
| 2014/0277337 A1* | 9/2014 | Chen | A61L 29/06 623/1.11 |
| 2015/0105506 A1* | 4/2015 | Benighaus | C08K 5/005 524/222 |

FOREIGN PATENT DOCUMENTS

| | | |
|---|---|---|
| JP | H01266163 A | 10/1989 |
| JP | H02208359 A | 8/1990 |
| WO | 01/72903 A2 | 10/2001 |

OTHER PUBLICATIONS

PCT/US2017/040926, The International Search Report and the Written Opinion of the International Searching Authority, dated Oct. 24, 2017, pp. 1-13.

\* cited by examiner

*Primary Examiner* — Michael F Pepitone (57) ABSTRACT

A plasticized nylon and a medical device including plasticized nylon. The medical device may be a dilatation balloon. Also disclosed are methods of plasticizing nylon.

15 Claims, 3 Drawing Sheets

MEDICAL DEVICE AND PLASTICIZED NYLON MATERIAL

CONTINUING APPLICATION DATA

This application claims the benefit of U.S. Provisional Application Ser. No. 62/359,323, filed Jul. 7, 2016, which is incorporated by reference herein.

BACKGROUND

Many medical devices, particularly balloons and catheters used in angioplasty procedures are made from polyamides such as various nylons. Such polymers are often relatively stiff for some delivery systems and processes.

The unique conditions under which balloon dilatation is performed typically require extremely thin-walled, high-strength balloons that, when deflated, are flexible and trackable enough to be maneuvered through small, tortuous vessels. Balloons made from high-strength polymers, while exhibiting high burst strengths, exhibit less flexibility and trackability than desired. The addition of a plasticizer to the materials increases the softness and flexibility of the balloon; however, the use of plasticizer can limit the balloon's applicability as a bio-compatible material. Balloons that exhibit high burst strengths that can be used in stent delivery but also exhibit high flexibility and trackability are desired. New balloon materials are therefore needed to tailor the properties of the balloon and produce high-strength and highly flexible balloons for medical applications.

SUMMARY OF THE INVENTION

In one aspect, this disclosure describes a medical device including plasticized nylon. In another aspect, this disclosure describes a plasticized nylon. The plasticized nylon includes a nylon and a plasticizer. In a further aspect, this disclosure describes a method of plasticizing nylon, the method including compounding a nylon with a plasticizer.

In some embodiments, the plasticizer includes a plasticizer having the following structure:

wherein R is a C2-C16 hydrocarbon.

In some embodiments, the plasticizer includes

In some embodiments, the plasticizer includes IRGANOX 1098.

In some embodiments, the nylon includes a nylon copolymerized with a polyether. In some embodiments, the nylon is selected from Nylon-6, Nylon-7, Nylon-8, Nylon-9, Nylon-10, Nylon-11, Nylon-12, Nylon-13, Nylon-14, Nylon-15, Nylon-16, Nylon-17, Nylon-18, Nylon-6,6, Nylon-6,8, Nylon-6,10, Nylon-6,12, Nylon-6,14, Nylon-8,8, Nylon-8,10, Nylon-8,12, Nylon-8,14, Nylon-10,10, Nylon-10,12, Nylon-8,12, Nylon-10,14, Nylon-12,12, Nylon-12,14, Nylon-14,16, and combinations thereof. In some embodiments, the nylon includes a block copolymer of polyether-co-Nylon-12.

In some embodiments, the plasticizer is present in an amount of greater than 1 weight percent (wt-%), based on the total weight of the plasticized nylon. In some embodiments, the plasticizer is present in an amount of up to 10 wt-%, based on the total weight of the plasticized nylon. In some embodiments, the plasticizer is present in an amount sufficient to decrease the flexural modulus of the nylon by at least 10 percent (%).

In some embodiments, the medical device includes a balloon including, for example, a dilatation balloon. In some embodiments, the medical device includes a catheter or medical tubing.

In some embodiments, the plasticized nylon is in the form of a film.

The term "plasticizer" is used herein to mean a material that can decrease the tensile modulus and/or flexural modulus of a polymer. The plasticizer may influence the morphology of the polymer and/or may affect (for example, decrease) the melting temperature and/or glass transition temperature.

The term "nylon" is used herein to mean a linear polymer with at least one amide bond in the main chain. Thus, as used herein, "nylon" refers to homopolymers or copolymers of various types of nylon, optionally copolymerized with polymers other than nylon (for example, polyether, polyurethane, polyester, polysiloxane, and the like). This includes diblock, triblock, segmented block copolymers including nylon.

The term "additive" is used herein to refer to any material added to the polymer to affect the polymer's (for example, balloon's) properties.

The words "preferred" and "preferably" refer to embodiments of the invention that may afford certain benefits, under certain circumstances. Other embodiments may also be preferred, however, under the same or other circumstances. Furthermore, the recitation of one or more preferred embodiments does not imply that other embodiments are not useful, and is not intended to exclude other embodiments from the scope of the invention.

The terms "comprises" and variations thereof do not have a limiting meaning where these terms appear in the descrip tion and claims. Such terms will be understood to imply the inclusion of a stated step or element or group of steps or elements but not the exclusion of any other step or element or group of steps or elements. By "consisting of" is meant including, and limited to, whatever follows the phrase "consisting of." Thus, the phrase "consisting of" indicates that the listed elements are required or mandatory, and that no other elements may be present. By "consisting essentially of" is meant including any elements listed after the phrase, and limited to other elements that do not interfere with or contribute to the activity or action specified in the disclosure for the listed elements. Thus, the phrase "consisting essentially of" indicates that the listed elements are required or mandatory, but that other elements are optional and may or may not be present depending upon whether or not they materially affect the activity or action of the listed elements.

Unless otherwise specified, "a," "an," "the," and "at least one" are used interchangeably and mean one or more than one.

Also herein, the recitations of numerical ranges by endpoints include all numbers subsumed within that range (for example, 1 to 5 includes 1, 1.5, 2, 2.75, 3, 3.80, 4, 5, etc.).

For any method disclosed herein that includes discrete steps, the steps may be conducted in any feasible order. And, as appropriate, any combination of two or more steps may be conducted simultaneously.

Unless otherwise indicated, all numbers expressing quantities of components, molecular weights, and so forth used in the specification and claims are to be understood as being modified in all instances by the term "about." Accordingly, unless otherwise indicated to the contrary, the numerical parameters set forth in the specification and claims are approximations that may vary depending upon the desired properties sought to be obtained by the present invention. At the very least, and not as an attempt to limit the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. All numerical values, however, inherently contain a range necessarily resulting from the standard deviation found in their respective testing measurements.

All headings are for the convenience of the reader and should not be used to limit the meaning of the text that follows the heading, unless so specified.

The above summary of the present invention is not intended to describe each disclosed embodiment or every implementation of the present invention. The description that follows more particularly exemplifies illustrative embodiments. In several places throughout the application, guidance is provided through lists of examples, which examples can be used in various combinations. In each instance, the recited list serves only as a representative group and should not be interpreted as an exclusive list.

DETAILED DESCRIPTION

It is desirable to improve the flexibility and trackability of dilatation balloons while maintaining a high degree of strength in the balloon. An ideal balloon is strong and yet flexible. The strength of the material provides high burst pressure, while the flexibility gives better deliverability. Improved flexibility and trackability allow a surgeon to maneuver the balloon, and alternatively, a balloon and stent, through very small diameter vasculature that may have a large degree of blockage or plaque build-up. The high degree of strength provides the surgeon with maximum flexibility to inflate the balloon, and alternatively, to deliver a stent upon inflation, without bursting the balloon.

This disclosure describes a plasticized nylon that includes nylon and a plasticizer having the following structure:

wherein R is a C2-C16 hydrocarbon. One such plasticizer is IRGANOX 1098. This disclosure also describes medical devices including, for example, dilatation balloons that include the plasticized nylon.

A plasticizer may be added to nylon to improve the flexibility of nylon-containing balloons. Disclosed herein is the surprising discovery that an anti-oxidant material, having the following structure:

wherein R is a C2-C16 hydrocarbon, can be used as a plasticizer for a nylon including, for example, for a PEBAX material, that is, a block copolymer of polyether and nylon. Generally, adding a plasticizer decreases the tensile strength of a polymer. In contrast, the use of an anti-oxidant material, having the following structure:

wherein R is a C2-C16 hydrocarbon, as a plasticizer, as described herein, decreases the flexural modulus of the polymer while maintaining its tensile strength. For example, the use of the anti-oxidant material IRGANOX 1098 as a plasticizer decreases the flexural modulus of the polymer while maintaining its tensile strength.

The chemical structure of IRGANOX 1098 is shown below:

Anti-oxidant materials including, for example, IRGANOX 1098 are typically added to polyamide resins as an anti-oxidant material and, as an anti-oxidant material, are used in an amount of no more than 1%. In contrast to a plasticizer—which is added to improve flexibility of a polymer—the purpose of an anti-oxidant is to protect a polymer from degradation during processing, storage, and service. At the time of the invention, no literature suggested that an anti-oxidant material, having the following structure:

wherein R is a C2-C16 hydrocarbon, could be used as a plasticizer for nylon, generally, or for PEBAX materials, specifically. Similarly, no literature suggested using IRGANOX 1098 as a plasticizer for nylon, generally, or for PEBAX materials, specifically.

In some embodiments, the C2-C16 hydrocarbon can include, for example, an alkylene group, an alkenylene group, an alkynylene group, etc. In some embodiments, the C2-C16 hydrocarbon includes an alkylene group. The term "alkylene group" means a saturated linear or branched hydrocarbon group including, for example, ethylene, isopropylene, t-butylene, heptylene, dodecylene, octadecylene, amylene, 2-ethylhexylene, and the like. The term "alkenylene group" means an unsaturated, linear or branched hydrocarbon group with one or more carbon-carbon double bonds, such as a vinyl group. The term "alkynyl group" means an unsaturated, linear or branched hydrocarbon group with one or more carbon-carbon triple bonds.

In some embodiments, the plasticizer is present in an amount (based on the total weight of the plasticized nylon) of greater than 1 weight percent (wt-%), at least 1.5 wt-%, at least 2 wt-%, at least 2.5 wt-%, at least 3 wt-%, at least 4 wt-%, or at least 5 wt-%. In some embodiments, the plasticizer is present in an amount (based on the total weight of the plasticized nylon) of up to 5 wt-%, up to 7 wt-%, up to 10 wt-%, up to 15 wt-%, or up to 20 wt-%. For example, the plasticizer may be present in an amount (based on the total weight of the plasticized nylon) of greater than 1 wt-% and up to 10 wt-%. In an exemplary embodiment, the plasticizer may be present in an amount (based on the total weight of the plasticized nylon) of at least 2.5 wt-% and up to 10 wt-%.

In some embodiments, the plasticizer is present in an amount sufficient to decrease the flexural modulus of the nylon by at least 10%, at least 12%, at least 14%, at least 16%, at least 18%, at least 20%, at least 22%, at least 24%, at least 28%, or at least 30%.

The nylon may include any suitable nylon including, for example, any nylon suitable for use in medical devices. In certain embodiments, the nylon may be selected from the group of Nylon-6, Nylon-7, Nylon-8, Nylon-9, Nylon-10, Nylon-11, Nylon-12, Nylon-13, Nylon-14, Nylon-15, Nylon-16, Nylon-17, Nylon-18, Nylon-6,6, Nylon-6,8, Nylon-6,10, Nylon-6,12, Nylon-6,14, Nylon-8,8, Nylon-8,10, Nylon-8,12, Nylon-8,14, Nylon-10,10, Nylon-10,12, Nylon-8,12, Nylon-10,14, Nylon-12,12, Nylon-12,14, Nylon-14,16, and combinations thereof. In certain embodiments, the nylon may be selected from the group of Nylon-6, Nylon-11, Nylon-12, Nylon-6,6, Nylon-6,10, and combinations thereof.

The nylon can be copolymerized with other polymers, such as polyether, for example. Block copolymers of the nylons such as polyether-co-Nylon-12 can be used if desired. In some embodiments, the nylon includes a member of the PEBAX family of polymers with various polyether (poly(tetramethylene oxide)) compositions produced by Arkema Inc. Such examples include PEBAX 7233, PEBAX 7033, PEBAX 6333, PEBAX 4033, PEBAX 3533, PEBAX 2533, PEBAX 5533, etc. Other examples of nylon-including polymers which are within the scope of "nylon" as used herein, include polyurethane-block-nylon, polyester-block-nylon, and polysiloxane-block-nylon.

In certain embodiments, the nylon is copolymerized with a polyether. In some embodiments, the nylon includes a block copolymer of polyether-co-Nylon-12.

In certain embodiments, the number average molecular weight of the nylon may be at least 5,000 Daltons and no more than 5,000,000 Daltons. In the case of nylon block copolymers, the non-nylon block may have a number average molecular weight between 500 Daltons and 1,000,000 Daltons.

In another aspect, this disclosure describes a method of plasticizing a nylon with a plasticizer having the following structure:

wherein R is a C2-C16 hydrocarbon. In some embodiments, the plasticizer includes IRGANOX 1098. The nylon and plasticizer can be combined using a variety of techniques including, for example, by compounding. Compounding may include blending and/or mixing. In some embodiments, compounding may be performed in a mixer such as an extrusion machine (also referred to as an extruder). In some embodiments, compounding may be performed at a temperature greater than the melting point of the nylon and/or at a temperature greater than the glass transition temperature of the nylon. As illustrated by Example 1, nylon (for example, PEBAX 7033, PEBAX 6333, or PEBAX 5533) can be blended with IRGANOX 1098 in a melt at 200° C. In some embodiments, nylon can be blended with the plasticizer at a temperature of at least 170° C., at least 180° C., at least 190° C., or at least 200° C. In some embodiments, nylon can be blended with the plasticizer at a temperature of up to 240° C., up to 250° C., up to 260° C., up to 270° C., or up to 280° C. For example, in some embodiments, nylon can be blended with the plasticizer at a temperature in a range of 180° C. to 270° C. As illustrated by Example 2, nylon (for example, PEBAX 7033) can be compounded with IRGANOX 1098 in a twin extruder.

The thermal and mechanical analysis of the plasticized nylon (including, for example, a compounded resin) shows the effectiveness of IRGANOX 1098 as a plasticizer (see, for example, Examples 1 and 2). For example, as shown in Example, 2, within the range of 2.5 wt-% to 10 wt-% of IRGANOX 1098, the plasticized polymers retained the tensile strength of the base material (PEBAX 7033), while the flexural modulus decreased with increasing plasticizer level. These results indicate that the material became softer while its mechanical strength was maintained, properties that are very desirable for applications such as angioplasty balloons. The mechanical strength is desirable for high burst pressure and low profile, while the high flexibility is desirable for deliverability.

The plasticized nylon of the present disclosure may include one or more additives. Examples of additives include fillers such as tungsten, barium sulfate, bismuth sub carbonate and inorganic nanoparticles, antioxidants, colorants, crosslinking agents, impact strength modifiers, and combinations thereof.

The plasticized nylon of the present disclosure can be used in a variety of medical devices or portions thereof. In some embodiments, the medical device includes a balloon. Examples of medical devices and/or balloons include, but are not limited to, a dilatation balloon, a stent delivery balloon, a positioning balloon, a diagnostic balloon, an occlusion balloon, a multifunctional balloon, a multilumen balloon, a cryoballoon, a light therapy balloon, an ablation balloon including an atrial fibrillation (AF) balloon and a renal denervation balloon, a heat transfer balloon, an inner member, a distal tip, medical tubing, or a catheter. Other medical devices include structural heart devices; orthopedic and spinal devices; drug delivery devices including, for example, an insulin pump; neural devices; a pacemaker; an implantable cardioverter defibrillator; surgery devices; pulmonary devices; thrombus removal devices; endoscope devices; etc. In some embodiments, the plasticized nylon in the medical device is present in the form of a film.

In certain embodiments, the plasticized nylon is used in a balloon or medical tubing. In certain embodiments, the plasticized nylon is used in a balloon or catheter.

In one embodiment, the present disclosure provides a dilatation balloon catheter that includes: a tubular elongated catheter shaft having proximal and distal portions; and a dilatation balloon disposed on said shaft, wherein the shaft and/or balloon includes a plasticized nylon of the present disclosure.

Figure 1:
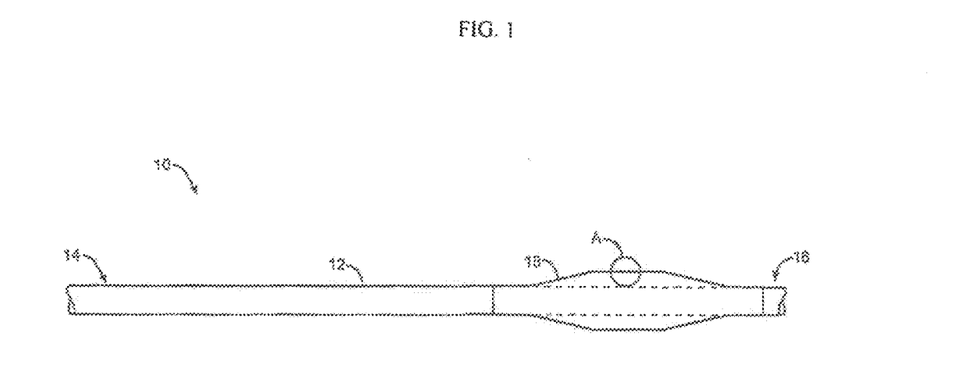
FIG. 1 shows a schematic side view of a dilatation balloon catheter according to an embodiment of the present disclosure.

A dilatation balloon catheter 10 (herein also referred to as "catheter") according to one embodiment of the disclosure is illustrated in FIG. 1. As illustrated, the catheter 10 includes a tubular elongated catheter shaft 12 (herein also referred to as "catheter shaft" or "shaft") having a proximal portion 14 and a distal portion 16, and a dilatation balloon 18 disposed on or otherwise connected to the distal portion 16 of the shaft 12. The balloon 18 can have a wall (a portion of which is designated by "A") that includes a single layer or dual layer of polymeric materials, for example. The wall can include therapeutic agents or biologically active materials (for example, antiproliferative agents such as rapamycin and its derivatives, paclitaxel and its derivatives, anti-inflammatory agents, and anti-thrombogenic agents) disposed thereon, optionally with one or more other additives or polymeric coatings.

Dilatation is used herein to refer to the expandability of the balloon. In certain embodiments, balloons of the present disclosure are expandable 2% to 40% greater than the original balloon size. In some embodiments, the expandability of the balloon may be in the range of 5% to 20%.

Figure 2:
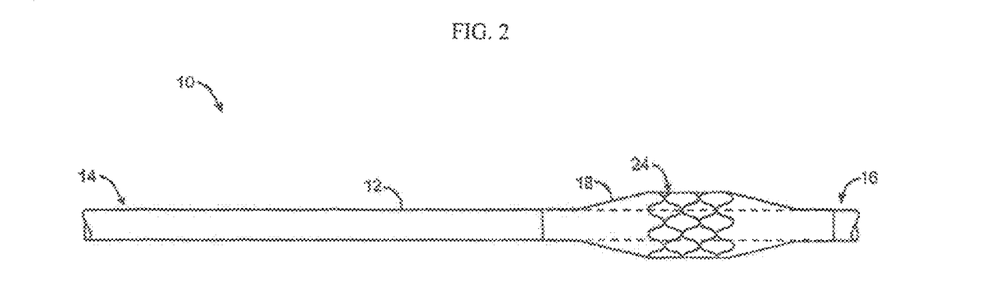
FIG. 2 shows a schematic side view of a stent delivery catheter according to another embodiment of the present disclosure.

With reference to FIG. 2, dilatation balloon catheter 10, as described in FIG. 1 and including a balloon 18 of the present disclosure can optionally further include a stent 24 disposed on the balloon 18. The balloon 18 may have high hoop strengths and allow for expanded delivery of the stent upon inflation of the balloon without bursting or puncturing the balloon. The stent 24 may optionally include a therapeutic agent or biologically active material. Any therapeutic agent or biologically active material, as described above, can be used in the stent. Specific examples include, but are not limited to, corticosteroids, such as dexamethasone, immunosuppressants, such as everolimus, sirolimus, and tacrolimus, zotarolimus, and chemotherapeutic agents, such as paclitaxel. The therapeutica gent or biologically active material may elute out of the stent and into the surrounding tissue over a controlled and predictable time.

As those skilled in the art will appreciate, the use of the plasticizers disclosed herein including, for example, IRGANOX 1098, may also be very useful beyond medical applications, based upon the data presented. The non-medical applications of such materials include, but are not limited to, fuel line, tubing for hydraulic clutches, vacuum line, tubing for diesel fuel lines permanently exposed to high temperature, extrusion coating for metal tubing, air brake tubing, sheath of electric cable, flexible tubing for pneumatic systems, electrical wire insulation, quick disconnectors, precision molding parts with isotropic shrinkages, sportswear, etc.

ILLUSTRATIVE EMBODIMENTS

Medical Device Embodiments
1. A medical device comprising plasticized nylon, wherein the plasticized nylon comprises a nylon and a plasticizer, the plasticizer comprising a plasticizer having the following structure:

wherein R is a C2-C16 hydrocarbon.

2. The medical device of embodiment 1 wherein the C2-C16 hydrocarbon comprises at least one of an alkylene group, an alkenylene group, and an alkynylene group.

3. The medical device of any one of the preceding embodiments wherein the C2-C16 hydrocarbon comprises an alkylene group.

4. The medical device of embodiment 1 wherein the plasticizer comprises:

5. The medical device of any one of the preceding embodiments wherein the nylon comprises a nylon copolymerized with a polyether.

6. The medical device of any one of the preceding embodiments wherein the nylon is selected from Nylon-6, Nylon-7, Nylon-8, Nylon-9, Nylon-10, Nylon-11, Nylon-12, Nylon-13, Nylon-14, Nylon-15, Nylon-16, Nylon-17, Nylon-18, Nylon-6,6, Nylon-6,8, Nylon-6,10, Nylon-6,12, Nylon-6,14, Nylon-8,8, Nylon-8,10, Nylon-8,12, Nylon-8,14, Nylon-10,10, Nylon-10,12, Nylon-8,12, Nylon-10,14, Nylon-12,12, Nylon-12,14, Nylon-14,16, and combinations thereof.

7. The medical device of any one of the preceding embodiments wherein the nylon comprises a block copolymer of polyether-co-Nylon-12.

8. The medical device of any one of the preceding embodiments wherein the plasticizer is present in an amount of greater than 1 wt-%, at least 1.5 wt-%, at least 2 wt-%, at least 2.5 wt-%, at least 3 wt-%, at least 4 wt-%, or at least 5 wt-%, based on the total weight of the plasticized nylon.

9. The medical device of any one of the preceding embodiments wherein the plasticizer is present in an amount of up to 5 wt-%, up to 7 wt-%, up to 10 wt-%, up to 15 wt-%, or up to 20 wt-%, based on the total weight of the plasticized nylon.

10. The medical device of any one of the preceding embodiments wherein the plasticizer is present in an amount of greater than 1 wt-% and up to 10 wt-%, based on the total weight of the plasticized nylon.

11. The medical device of any one of the preceding embodiments wherein the plasticizer is present in an amount sufficient to decrease the flexural modulus of the nylon by at least 10%, at least 12%, at least 14%, at least 16%, at least 18%, at least 20%, at least 22%, at least 24%, at least 28%, or at least 30%.

12. The medical device of any one of the preceding embodiments wherein the medical device comprises a balloon.

13. The medical device of embodiment 12 wherein the balloon is a dilatation balloon.

14. The medical device of any one of the preceding embodiments wherein the medical device comprises a catheter or medical tubing.

15. The medical device of any one of the preceding embodiments wherein the plasticized nylon is in the form of a film.

Plasticized Nylon Embodiments
1. A plasticized nylon comprising a nylon and a plasticizer, the plasticizer comprising a plasticizer having the following structure:

wherein R is a C2-C16 hydrocarbon.

2. The plasticized nylon of embodiment 1 wherein the C2-C16 hydrocarbon comprises at least one of an alkylene group, an alkenylene group, and an alkynylene group.

3. The plasticized nylon of any one of the preceding embodiments wherein the C2-C16 hydrocarbon comprises an alkylene group.

4. The plasticized nylon of embodiment 1 wherein the plasticizer comprises:

5. The plasticized nylon of any one of the preceding embodiments wherein the nylon comprises a nylon copolymerized with a polyether.

6. The plasticized nylon of any one of the preceding embodiments wherein the nylon is selected from Nylon-6, Nylon-7, Nylon-8, Nylon-9, Nylon-10, Nylon-11, Nylon-12, Nylon-13, Nylon-14, Nylon-15, Nylon-16, Nylon-17, Nylon-18, Nylon-6,6, Nylon-6,8, Nylon-6,10, Nylon-6,12, Nylon-6,14, Nylon-8,8, Nylon-8,10, Nylon-8,12, Nylon-8,14, Nylon-10,10, Nylon-10,12, Nylon-8,12, Nylon-10,14, Nylon-12,12, Nylon-12,14, Nylon-14,16, and combinations thereof.

7. The plasticized nylon of any one of the preceding embodiments wherein the nylon comprises a block copolymer of polyether-co-Nylon-12.

wherein R is a C2-C16 hydrocarbon.

2. The method of embodiment 1 wherein the C2-C16 hydrocarbon comprises at least one of an alkylene group, an alkenylene group, and an alkynylene group.

3. The method of any one of the preceding embodiments wherein the C2-C16 hydrocarbon comprises an alkylene group.

4. The method of embodiment 1 wherein the plasticizer comprises:

8. The plasticized nylon of any one of the preceding embodiments wherein the plasticizer is present in an amount of greater than 1 wt-%, at least 1.5 wt-%, at least 2 wt-%, at least 2.5 wt-%, at least 3 wt-%, at least 4 wt-%, or at least 5 wt-%, based on the total weight of the plasticized nylon.

9. The plasticized nylon of any one of the preceding embodiments wherein the plasticizer is present in an amount of up to 5 wt-%, up to 10 wt-%, up to 15 wt-%, or up to 20 wt-%, based on the total weight of the plasticized nylon.

10. The plasticized nylon of any one of the preceding embodiments wherein the plasticizer is present in an amount of greater than 1 wt-% and up to 10 wt-%, based on the total weight of the plasticized nylon.

11. The plasticized nylon of any one of the preceding embodiments wherein the plasticizer is present in an amount sufficient to decrease the flexural modulus of the nylon by at least 10%, at least 12%, at least 14%, at least 16%, at least 18%, at least 20%, at least 22%, at least 24%, at least 28%, or at least 30%.

Method Embodiments

1. A method of plasticizing nylon, the method comprising compounding a nylon with a plasticizer, the plasticizer comprising a plasticizer having the following structure:

5. The method of any one of the preceding embodiments wherein compounding the nylon and plasticizer comprises blending the nylon and plasticizer in a melt at a temperature of at least 170° C., at least 180° C., at least 190° C., or at least 200° C., and of up to 240° C., up to 250° C., up to 260° C., up to 270° C., or up to 280° C.

6. The method of any one of the preceding embodiments wherein compounding the nylon and the plasticizer comprises extrusion.

7. The method of any one of the preceding embodiments wherein the nylon and the plasticizer are compounded at a temperature greater than the melting point of the nylon.

8. The method of any one of the preceding embodiments wherein the nylon and the plasticizer are compounded at a temperature greater than the glass transition temperature of the nylon.

9. The method of any one of the preceding embodiments wherein the plasticizer is present in an amount of greater than 1 wt-%, at least 1.5 wt-%, at least 2 wt-%, at least 2.5 wt-%, at least 3 wt-%, at least 4 wt-%, or at least 5 wt-%, based on the total weight of the plasticized nylon.

10. The method of any one of the preceding embodiments wherein the plasticizer is present in an amount of up to 5 wt-%, up to 10 wt-%, up to 15 wt-%, or up to 20 wt-%, based on the total weight of the plasticized nylon.

11. The method of any one of the preceding embodiments wherein the plasticizer is present in an amount of greater than 1 wt-% and up to 10 wt-%, based on the total weight of the plasticized nylon.

12. The method of any one of the preceding embodiments wherein the nylon comprises a nylon copolymerized with a polyether.

13. The method of any one of the preceding embodiments wherein the nylon is selected from Nylon-6, Nylon-7, Nylon-8, Nylon-9, Nylon-10, Nylon-11, Nylon-12, Nylon-13, Nylon-14, Nylon-15, Nylon-16, Nylon-17, Nylon-18, Nylon-6,6, Nylon-6,8, Nylon-6,10, Nylon-6,12, Nylon-6,14, Nylon-8,8, Nylon-8,10, Nylon-8,12, Nylon-8,14, Nylon-10,10, Nylon-10,12, Nylon-8,12, Nylon-10,14, Nylon-12,12, Nylon-12,14, Nylon-14,16, and combinations thereof.

14. The method of any one of the preceding embodiments wherein the nylon comprises a block copolymer of polyether-co-Nylon-12.

The present invention is illustrated by the following examples. It is to be understood that the particular examples, materials, amounts, and procedures are to be interpreted broadly in accordance with the scope and spirit of the invention as set forth herein.

EXAMPLES

Example 1

In a glass reactor, 95 parts of PEBAX 7033 was blended with 5 parts of anti-oxidant IRGANOX 1098 in the melt at 200° C. The blend resin (PEBAX 7033-IRG) was pressed into a 0.030 inch film and its mechanical properties were tested on an Instron machine according to ASTM 638 for tensile properties and ASTM D790-97B for flexural properties.

Similar blends (PEBAX 6333-IRG and PEBAX 5533-IRG) were made from PEBAX 6333 and PEBAX 5533 materials and IRGANOX 1098.

The control samples of PEBAX 7033, PEBAX 6333, and PEBAX 5533 were prepared under the same conditions.

Figure 3:
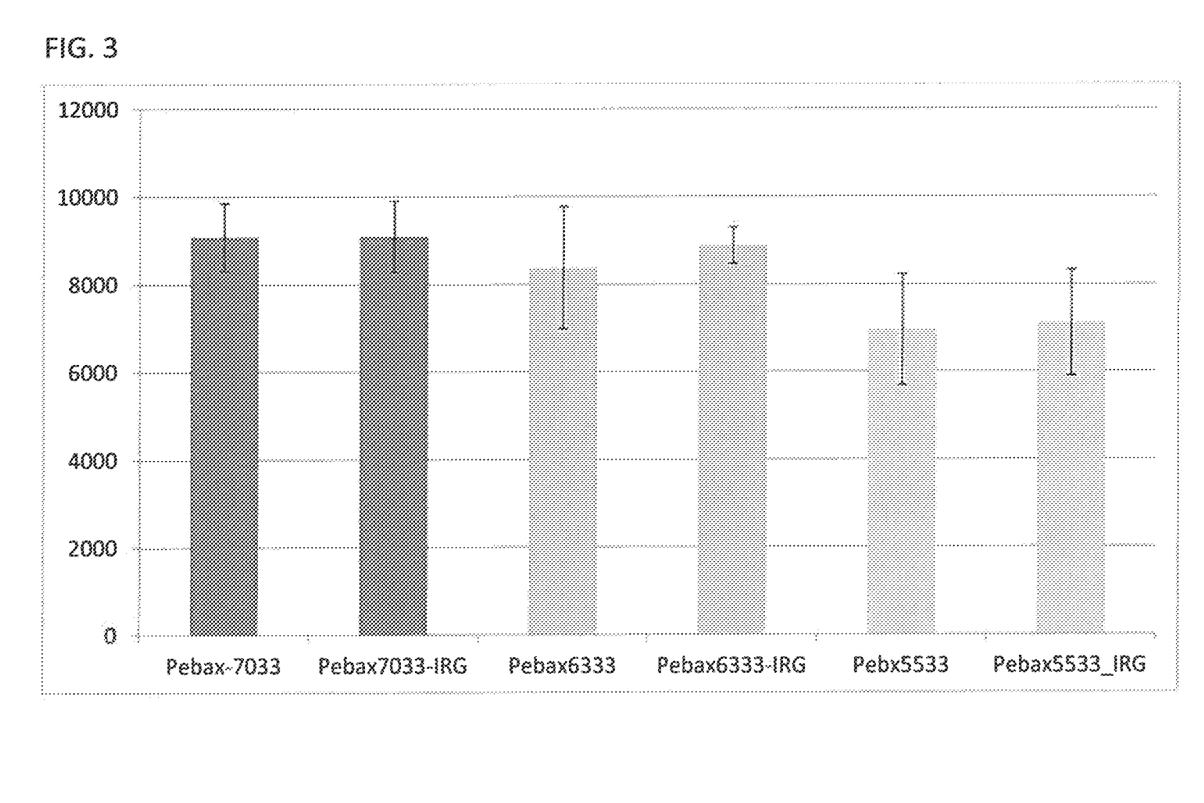
FIG. 3 shows a graph of tensile strength (pounds per square inch (psi)) of exemplary PEBAX materials compared with exemplary PEBAX materials blended with 5 weight percent (wt-%) IRGANOX 1098 (IRG). The error bars indicate the 95 percent (%) confidence interval.
Figure 4:
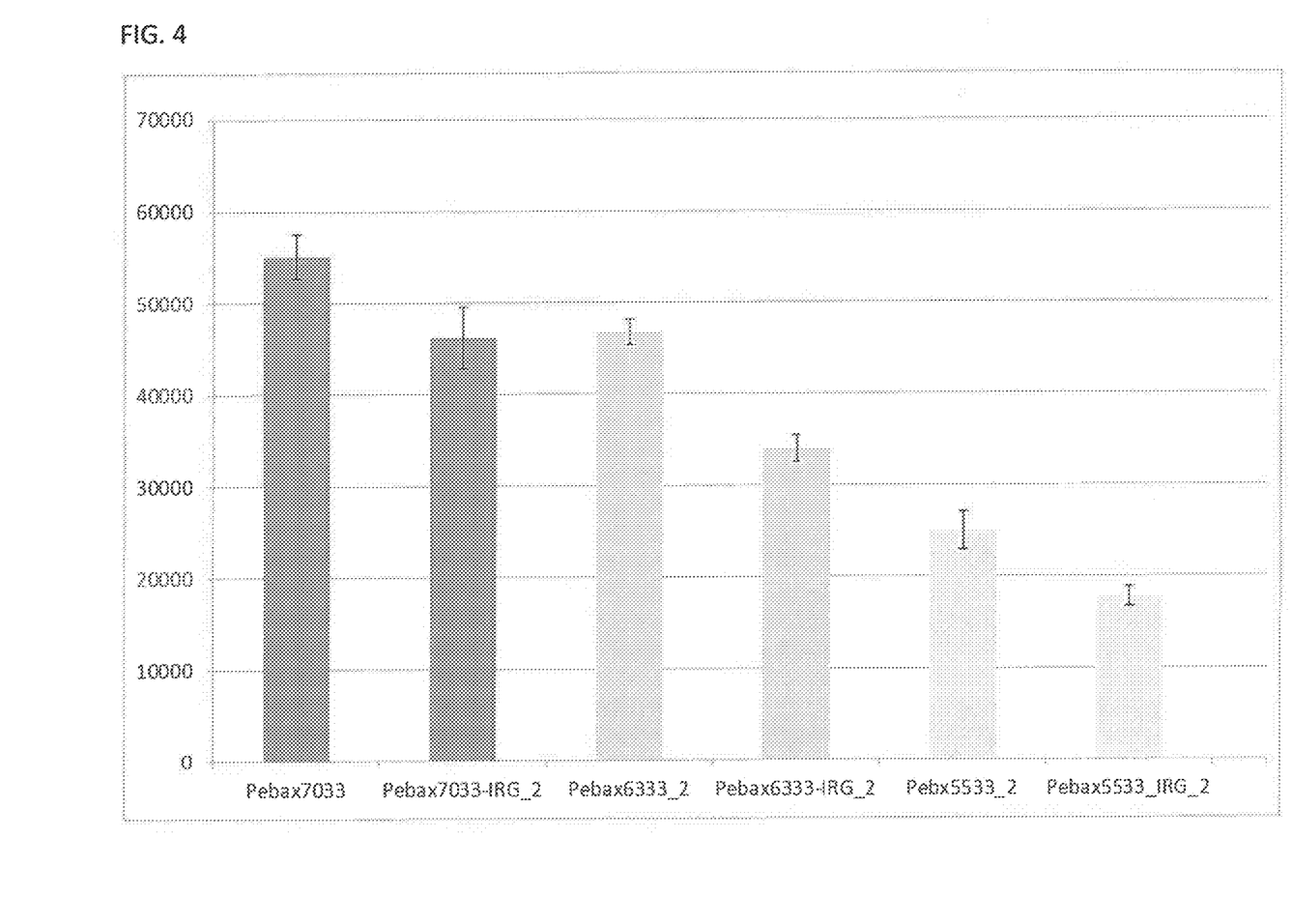
FIG. 4 shows the flexural modulus ((pounds per square inch (psi)) of exemplary compounded resins (Example 1). The error bars indicate the 95% confidence interval.

The mechanical properties are shown in FIG. 3 (tensile strength) and FIG. 4 (flexural modulus). Within experiment errors, no decrease in the tensile strength (FIG. 3) was observed. These results contrasted with the effect seen when adding most plasticizers because plasticizers generally decrease the tensile strength of a material. A significant decrease in flexural modulus of the compounded materials was observed, however (FIG. 4).

Example 2

PEBAX 7033 was compounded with 2.5%, 5.0%, 7.5%, and 10% by weight IRGANOX 1098 with a twin extruder. The mechanical properties were tested as in Example 1. The results are presented in Tables 1 and 2.

The results suggest the tensile strength of the base material (PEBAX 7033) was maintained and the flexural modulus was significantly decreased by adding up to 10% by weight of IRGANOX 1098.

TABLE 1

Mean Tensile Properties.

| Description | Yield Elong. % | Break Elong. % | Yield Stress psi | Tensile Strength psi | Elastic Modulus psi |
|---|---|---|---|---|---|
| Pebax 7033 | 15.8 | 382 | 3390 | 9040 | 58,320 |
| P. 7033/IRG. 1098(2.5%) | 16.3 | 374 | 3370 | 8840 | 55,950 |
| P. 7033/IRG. 1098(7.5%) | 20.2 | 389 | 3340 | 9010 | 49,440 |
| P. 7033/IRG. 1098(10.0%) | 21.3 | 406 | 3250 | 9230 | 49,545 |

TABLE 2

Mean Flexural Properties.

| Description | Maximum Flex. Strain % | Flex. Extension at max. Stress in. | Flexural Strength psi | Flexural Elast. Modulus psi |
|---|---|---|---|---|
| Pebax 7033 | 8.54 | 0.164 | 2993 | 61,718 |
| P. 7033/IRG. 1098(2.5%) | 8.64 | 0.166 | 2637 | 54892 |
| P. 7033/IRG. 1098(7.5%) | 8.71 | 0.168 | 2395 | 47336 |
| P. 7033/IRG. 1098(10.0%) | 8.66 | 0.163 | 2221 | 42475 |

The complete disclosure of all patents, patent applications, and publications, and electronically available material cited herein are incorporated by reference. In the event that any inconsistency exists between the disclosure of the present application and the disclosure(s) of any document incorporated herein by reference, the disclosure of the present application shall govern. The foregoing detailed description and examples have been given for clarity of understanding only. No unnecessary limitations are to be understood therefrom. The invention is not limited to the exact details shown and described, for variations obvious to one skilled in the art will be included within the invention defined by the claims.

What is claimed is:

1. A medical device comprising plasticized nylon, wherein the medical device comprises a balloon, wherein the plasticized nylon comprises a nylon and a plasticizer, the plasticizer comprising a plasticizer having the following structure:

wherein R is a C2-C16 hydrocarbon, wherein the plasticizer is present in an amount of greater than 1 wt-%, based on the total weight of the plasticized nylon, and wherein the flexural modulus of the plasticized nylon is at least 10% less than the flexural modulus of the nylon.

2. The medical device of claim 1, wherein the plasticizer comprises:

3. The medical device of claim 1, wherein the nylon comprises a nylon copolymerized with a polyether.

4. The medical device of claim 1, wherein the nylon is selected from Nylon-6, Nylon-7, Nylon-8, Nylon-9, Nylon-10, Nylon-11, Nylon-12, Nylon-13, Nylon-14, Nylon-15, Nylon-16, Nylon-17, Nylon-18, Nylon-6,6, Nylon-6,8, Nylon-6,10, Nylon-6,12, Nylon-6,14, Nylon-8,8, Nylon-8,10, Nylon-8,12, Nylon-8,14, Nylon-10,10, Nylon-10,12, Nylon-10,14, Nylon-12,12, Nylon-12,14, Nylon-14,16, and combinations thereof.

5. The medical device of claim 1 wherein the nylon comprises a block copolymer of polyether-co-Nylon-12.

6. The medical device of claim 1 wherein the plasticizer is present in an amount of up to 10 wt-%, based on the total weight of the plasticized nylon.

7. The medical device of claim 1 wherein the plasticizer is present in an amount of greater than 5 wt-%, based on the total weight of the plasticized nylon.

8. The medical device of claim 1 wherein the balloon is a dilatation balloon.

9. The medical device of claim 1 wherein the plasticized nylon is in the form of a film.

10. A method of making a balloon suitable for use in a medical device, the method comprising:
    plasticizing nylon to form a plasticized nylon, the method comprising compounding a nylon with a plasticizer, the plasticizer comprising a plasticizer having the following structure:

wherein R is a C2-C16 hydrocarbon, wherein the plasticizer is present in an amount of greater than 1 wt-% and up to 10 wt-%, based on the total weight of the plasticized nylon, and wherein the flexural modulus of the plasticized nylon is at least 10% less than the flexural modulus of the nylon; and
    forming a balloon comprising the plasticized nylon.

11. The method of claim 10 wherein compounding the nylon and the plasticizer comprises extrusion.

12. The method of claim 11, wherein the balloon comprises a dilatation balloon, a stent delivery balloon, a positioning balloon, a diagnostic balloon, an occlusion balloon, a multifunctional balloon, a multilumen balloon, a cryoballoon, a light therapy balloon, an ablation balloon, or a heat transfer balloon.

13. The method of claim 11, wherein the plasticized nylon further comprises an additive.

14. The medical device of claim 1, wherein the plasticized nylon further comprises an additive.

15. The medical device of claim 1, wherein the balloon comprises a dilatation balloon, a stent delivery balloon, a positioning balloon, a diagnostic balloon, an occlusion balloon, a multifunctional balloon, a multilumen balloon, a cryoballoon, a light therapy balloon, an ablation balloon, or a heat transfer balloon.

* * * * *